United States Patent
Miranda et al.

(10) Patent No.: US 10,638,890 B2
(45) Date of Patent: May 5, 2020

(54) TOILET PAPER ENCLOSURE

(71) Applicants: Filipe S. Miranda, Delray Beach, FL (US); Edson Jose De Miranda, Delray Beach, FL (US)

(72) Inventors: Filipe S. Miranda, Delray Beach, FL (US); Edson Jose De Miranda, Delray Beach, FL (US)

( * ) Notice: Subject to any disclaimer, the term of this patent is extended or adjusted under 35 U.S.C. 154(b) by 290 days.

(21) Appl. No.: 15/620,955

(22) Filed: Jun. 13, 2017

(65) Prior Publication Data
US 2018/0353017 A1  Dec. 13, 2018

(51) Int. Cl.
| | | |
|---|---|---|
| *A61L 2/10* | (2006.01) | |
| *A47K 10/22* | (2006.01) | |
| *A47K 10/40* | (2006.01) | |
| *A47K 10/32* | (2006.01) | |
| *A47K 10/38* | (2006.01) | |

(52) U.S. Cl.
CPC ............ *A47K 10/22* (2013.01); *A47K 10/405* (2013.01); *A61L 2/10* (2013.01); *A47K 2010/3233* (2013.01); *A47K 2010/3253* (2013.01); *A47K 2010/389* (2013.01); *A61L 2202/11* (2013.01)

(58) Field of Classification Search
CPC .......... A61L 2/10; A47K 10/22; A47K 10/405
See application file for complete search history.

(56) References Cited

U.S. PATENT DOCUMENTS

| | | | | |
|---|---|---|---|---|
| 1,512,849 | A * | 10/1924 | Isham | A47K 10/38 |
| | | | | 225/67 |
| 3,920,394 | A | 11/1975 | Marrapodi | |
| 6,296,331 | B1 * | 10/2001 | Tramontina | A47K 10/424 |
| | | | | 312/34.1 |
| 7,021,030 | B1 | 4/2006 | Burns | |
| 9,122,056 | B1 * | 9/2015 | Lorenzo | G02B 27/028 |
| 2004/0069892 | A1 * | 4/2004 | Fida | A47K 10/38 |
| | | | | 242/560 |
| 2016/0150921 | A1 * | 6/2016 | Shea | A47K 10/38 |
| | | | | 242/598.3 |

FOREIGN PATENT DOCUMENTS

| | | |
|---|---|---|
| CN | 2505014 Y | 10/2001 |
| CN | 2513581 Y | 12/2001 |
| KR | 20150031990 A * | 3/2015 |
| WO | 2007036130 | 5/2007 |

OTHER PUBLICATIONS

English Abstract for KR 20150031990 A, Inventor: Lee (Year: 2015).*

* cited by examiner

Primary Examiner — Sean E Conley
(74) Attorney, Agent, or Firm — The Concept Law Group, PA; Scott D. Smiley; Scott M. Garrett (57) ABSTRACT

A toilet paper dispenser including a wall mounted toilet paper dispensing body entirely recessed within a building wall; at least one rod disposed within the wall mounted toilet paper dispensing body to support at least one toilet paper roll thereon; and a door hingedly coupled to a lateral edge of the wall mounted toilet paper dispensing body so to form an enclosure that encloses the at least one rod and the at least one toilet paper roll when the door is closed.

10 Claims, 10 Drawing Sheets

TOILET PAPER ENCLOSURE

FIELD OF THE INVENTION

The present invention relates generally to a toilet paper retention device, and, more particularly, relates to an enclosure recessed within a building wall that is operably configured to retain and store toilet paper.

BACKGROUND OF THE INVENTION

It is well-known to provide toilet paper holders for dispensing toilet paper proximate a toilet bowl. Known toilet paper holders typically include a toilet paper roll support rod disposed external to a building wall proximate the toilet bowl. Unfortunately, existing toilet paper dispensers are exposed to the external environment which, because the toilet paper dispenser is near the toilet bowl, can result in the toilet paper roll being exposed to contaminates from the toilet bowl, especially during flushing. Such contamination is unsanitary and undesirable.

Some known toilet paper dispensers enclose a portion of the toilet paper roll within a housing, but leave a portion of the toilet paper roll exposed to the external environment so that the user can access the toilet paper roll. Unfortunately, such areas of user access can also be areas for potential contamination from the toilet bowl. Additionally, most existing toilet paper holders do not provide an apparatus and/or method for sanitizing or disinfesting a toilet paper roll, which can provide an additional precautionary measure for toilet paper rolls that may have already been unknowingly contaminated. Use of contaminated toilet paper is certainly undesirable, unsanitary, and may expose users to potential negative health risks.

Some toilet paper dispensers are stand-alone devices, while other toilet paper dispensers are mounted to the wall. Such wall-mounted toilet paper dispensers are often complicated and complex to install, requiring specialized installation skills and tools. Further, existing wall-mounted toilet paper dispensers are mounted to the outer surface of the wall such that they are disposed outside of the wall and occupy space near the wall that could be reserved for other bathroom fixtures. Toilet paper dispensers can also be generally unattractive and often do not aesthetically match a bathroom decor.

Therefore, a need exists to overcome the problems with the prior art as discussed above.

SUMMARY OF THE INVENTION

The invention provides a sanitizing toilet paper enclosure that overcomes the hereinafore-mentioned disadvantages of the heretofore-known devices and methods of this general type.

With the foregoing and other objects in view, there is provided, in accordance with the invention, in combination with a building wall having a front surface and defining a recessed cavity, an improvement including a wall mounted toilet paper dispensing body disposed behind the front surface of the building wall and within the recessed cavity; at least one toilet paper roll support member disposed within the wall mounted toilet paper dispensing body and behind the front surface of the building wall to support at least one toilet paper roll thereon; and a door hingedly coupled to a lateral edge of the wall mounted toilet paper dispensing body so to form an enclosure that encloses the toilet paper roll support member and the toilet paper roll when the door is in a closed position along a door translation path.

In accordance with another feature, an embodiment of the present invention includes a UV light disposed to emit UV rays toward the toilet paper roll disposed on the toilet paper roll support member.

In accordance with another feature, an embodiment of the present invention further includes a hinge, the hinge hingedly coupled to the lateral edge of the wall mounted toilet paper dispensing body and the door operably configured to be rotatably placed in the door translation path about a vertical axis defined by the hinge.

In accordance with another feature of the present invention, the closed position along the door translation path includes the door disposed over an opening defined by the building wall into which a main storage body of the wall mounted toilet paper dispensing body is entirely recessed such that the door forms a seal over the opening to enclose the toilet paper roll support member and the toilet paper roll within the wall mounted toilet paper dispensing body and behind the front surface of the building wall.

In accordance with another feature of the present invention, the wall mounted toilet paper dispensing body defines an open face into the enclosure when the door is in an open position along the door translation path; and the door is dimensioned to entirely cover the open face to seal the enclosure when the door is in the closed position along the door translation path.

In accordance with yet another feature of the present invention, the wall mounted toilet paper dispensing body includes a pair of opposing sidewalls, each of the pair of opposing sidewalls entirely recessed within the building wall and defining a recessed channel disposed within the enclosure, the pair of opposing sidewalls each respectively configured to slideably and frictionally receive an end of the toilet paper roll support member in the recessed channel for securing the toilet paper roll support member to the wall mounted toilet paper dispensing body.

In accordance with another feature of the present invention, the recessed channel for each of the pair of opposing sidewalls includes a first channel portion and a second channel portion, the first channel portion disposed to permit movement of the toilet paper roll support member in a direction toward a rear wall of the toilet paper dispensing body and the second channel portion spanning from a distal end of the respective first channel portion in a direction toward a bottom wall of the wall mounted toilet paper dispensing body, each of the pair of opposing sidewalls defining the second channel portion sized and shaped to restrict movement of the toilet paper roll support member in the direction toward the rear wall of the toilet paper dispensing body.

In accordance with a further feature of the present invention, the recessed channel for each of the pair of opposing sidewalls is formed as a multiple toilet paper roll recessed channel with a first recessed channel portion, a second recessed channel portion, and an intermediate recessed channel portion continuous with and interposed between the first and second recessed channel portions, each of the first recessed channel portion and the second recessed channel portion including a first channel portion and a second channel portion, the first channel portion disposed to permit movement of the toilet paper roll support member in a direction toward the building wall and the second channel portion disposed to restrict movement of the toilet paper roll support member in the direction toward the building wall.

In accordance with yet another feature of the present invention, the door includes a door frame portion and a plate portion, the door frame portion defining an aperture dimensioned to reveal the plate portion to an external environment and the plate portion removeably couplable to the door frame portion such that when the plate portion is coupled to the door frame portion the door forms the enclosure when the door is closed.

In accordance with another feature, an embodiment of the present invention includes at least one toilet paper feed member coupled to the wall mounted toilet paper dispensing body so as to be disposed at least one of above and beneath the toilet paper roll supported on the toilet paper roll support member and operable to support a free end of a toilet paper panel of the toilet paper roll for readily gripping by a user when the door is opened.

In accordance with a further feature of the present invention, the toilet paper feed member is coupled to the wall mounted toilet paper dispensing body so as to be selectively pivoted toward the toilet paper roll and away from the toilet paper roll supported on the toilet paper roll support member.

In accordance with yet another feature, an embodiment of the present invention includes a sanitizing toilet paper dispenser with a building wall; a toilet paper dispensing body entirely recessed within the building wall; at least one toilet paper roll support member disposed within the toilet paper dispensing body to support at least one toilet paper roll thereon; and a door. In a further embodiment of the present invention, the door includes a door frame portion and a plate portion, the door frame portion defining an aperture dimensioned to reveal the plate portion to an external environment and the plate portion removeably couplable to the door frame portion; and hingedly coupled to an edge of the toilet paper dispensing body so to so as to be rotatably openable and forming an enclosure that encloses the toilet paper roll support member and the toilet paper roll when the door is closed and the plate portion is coupled to the door frame portion.

In accordance with a further feature, an embodiment of the present invention includes a UV light disposed to emit UV rays toward the toilet paper roll disposed on the toilet paper roll support member.

In accordance with another feature of the present invention, the wall mounted toilet paper dispensing body defines an open face into the enclosure when the door is opened; and the door is dimensioned to entirely cover the open face to seal the enclosure when the door is closed.

In accordance with another feature of the present invention, the wall mounted toilet paper dispensing body includes a pair of opposing sidewalls, each of the pair of opposing sidewalls recessed within the building wall and defining a recessed channel disposed to slideably and frictionally receive an end of the toilet paper roll support member therein for securing the toilet paper roll support member to toilet paper dispensing body.

In accordance with yet another feature of the present invention, the recessed channel for each of the pair of opposing sidewalls includes a first channel portion and a second channel portion, the first channel portion disposed to permit movement of the toilet paper roll support member in a direction toward the building wall and the second channel portion disposed to restrict movement of the toilet paper roll support member in the direction toward the building wall.

In accordance with yet a further feature, an embodiment of the present invention includes at least one toilet paper feed member coupled to the toilet paper dispensing body so as to be disposed at least one of above and beneath the toilet paper roll supported on the toilet paper roll support member and operable to support a free end of a toilet paper panel of the toilet paper roll for readily gripping by a user when the door is opened.

In accordance with another feature, an embodiment of the present invention includes a sanitizing toilet paper dispenser having a wall mounted toilet paper dispensing body recessed within a building wall; at least one toilet paper roll support member disposed within the wall mounted toilet paper dispensing body to support at least one toilet paper roll thereon; a UV light disposed to emit UV rays toward the toilet paper roll disposed on the toilet paper roll support member; a door: including a door frame portion and a plate portion, the door frame portion defining an aperture dimensioned to reveal the plate portion to an external environment and the plate portion removeably couplable to the door frame portion; and hingedly coupled to an edge of the wall mounted toilet paper dispensing body so to so as to be rotatably openable and forming an enclosure that encloses the toilet paper roll support member, the toilet paper roll, and the UV light when the door is closed and the plate portion is coupled to the door frame portion; and at least one toilet paper feed member coupled to the wall mounted toilet paper dispensing body so as to be disposed at least one of above and beneath the toilet paper roll supported on the toilet paper roll support member and operable to support a free end of a toilet paper panel of the toilet paper roll for readily gripping by a user when the door is opened.

In accordance with yet another feature of the present invention, the edge is a lateral edge; and the door is further hingedly coupled to the lateral edge of the toilet paper dispensing body so as to be rotatably openable about a vertical axis defined by a hinge disposed at the lateral edge.

In accordance with another feature of the present invention, when the door is closed, the door is disposed over an opening defined by the building wall into which the wall mounted toilet paper dispensing body is recessed such that the door forms a seal over the opening to enclose the toilet paper roll support member, the toilet paper roll, and the UV light within the wall mounted toilet paper dispensing body and behind the building wall.

Although the invention is illustrated and described herein as embodied in a sanitizing toilet paper enclosure, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the enclosure from a top end to a bottom end thereof.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient toilet paper dispenser and storage assembly. Embodiments of the invention provide a wall mounted toilet paper dispensing body that is at least substantially recessed within a building wall. In addition, embodiments of the invention provide at least one toilet paper roll supporting rod, and a door hingedly coupled to the wall mounted toilet paper dispensing body that forms an enclosure for the rod and the toilet paper roll when the door is closed. Further embodiments of the present invention also include a UV light enclosed within the wall mounted toilet paper dispensing body to sanitize the toilet paper roll. Other embodiments of the present invention provide for recessed channels within sidewalls of the wall mounted body that permit movement of the rod in one direction for receiving the rod into the enclosure and that restricts movement of the rod in another direction for locking the rod into the enclosure. Additional embodiments include a novel and non-obvious toilet paper feed rod disposed above or beneath the toilet paper roll and operable to support a free end of a toilet paper panel for permitting the user to readily grip the free end when use is desired. Embodiments of the present invention also include a door frame and a plate portion that allows decorative plates to be interchangeable to provide decorative variety to users and to allow users to match the toilet paper enclosure to the user's wall or floor.

Figure 1:
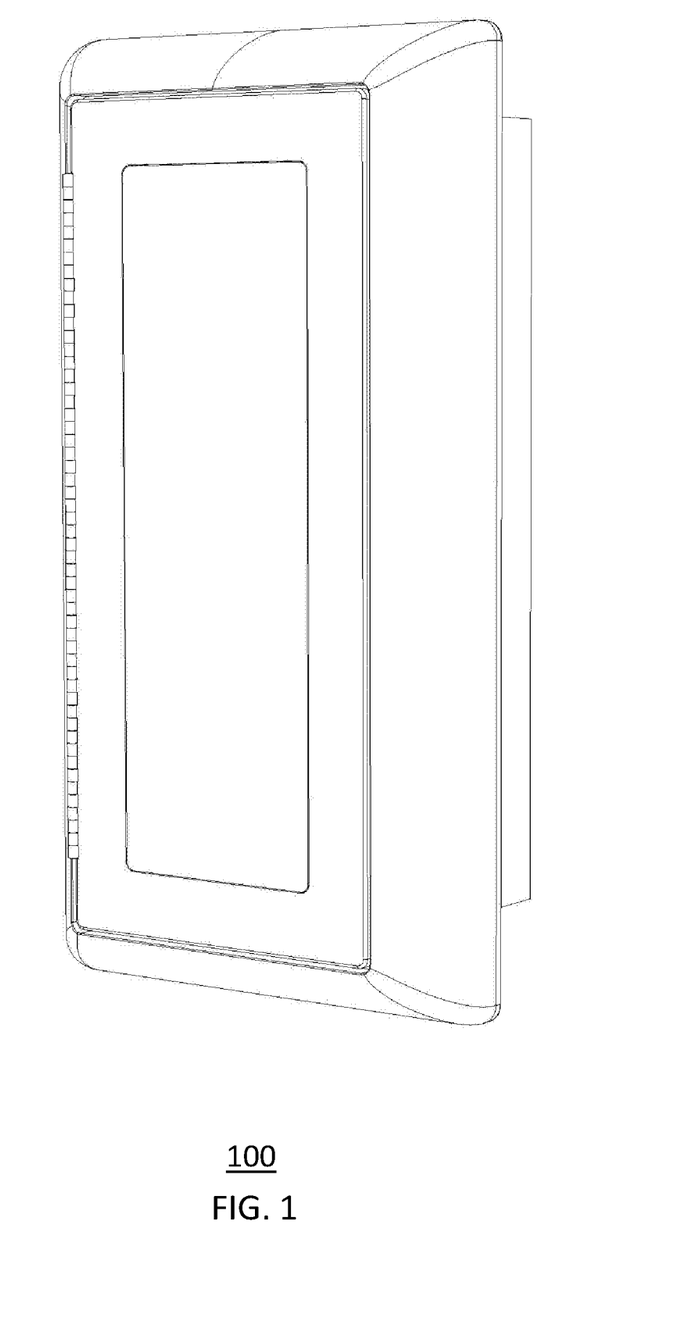
FIG. 1 is a front, perspective view of a toilet paper enclosure with a door closed, in accordance with an embodiment of the present invention.
Figure 2:
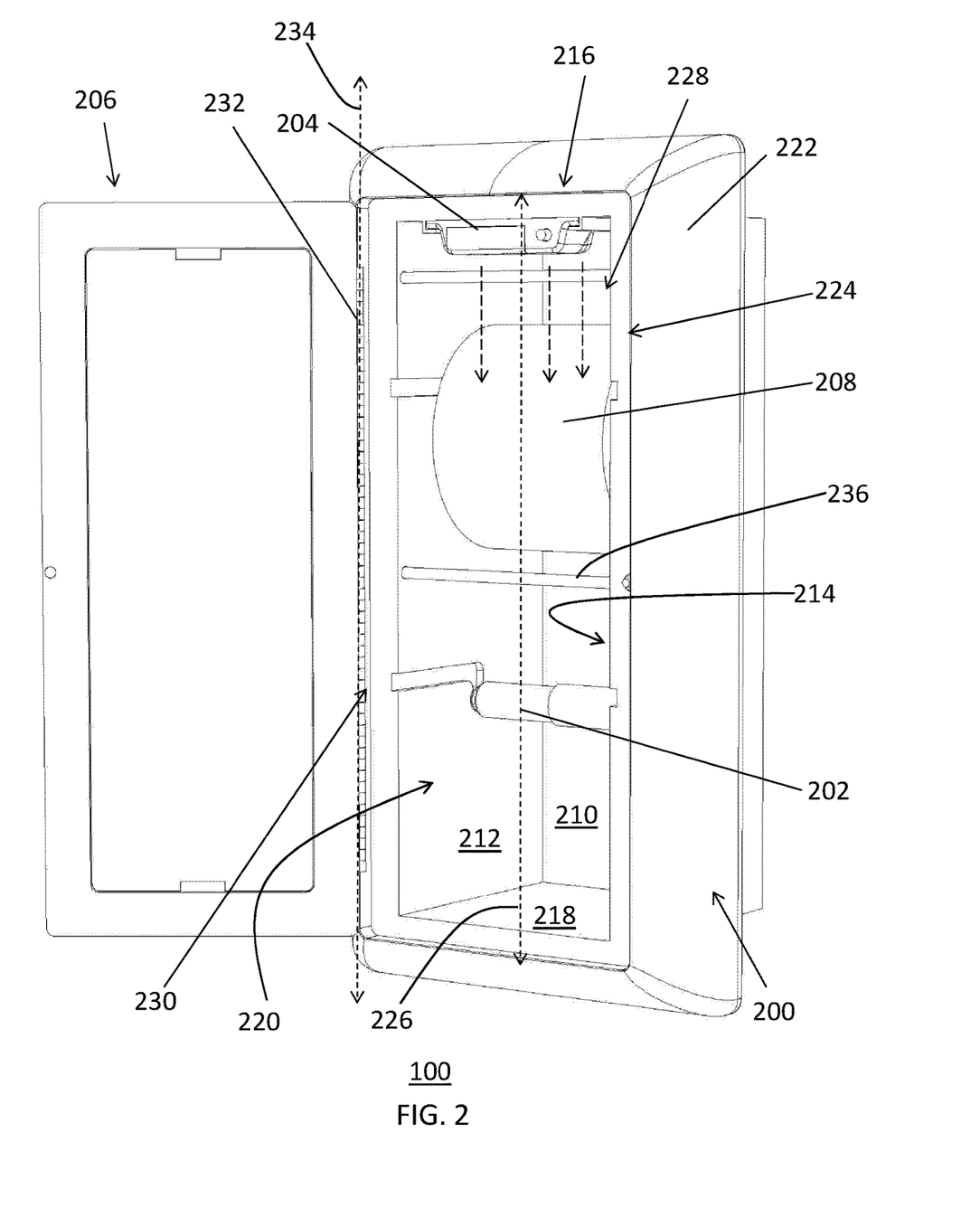
FIG. 2 is a front, perspective view of the toilet paper enclosure of FIG. 1 with the door opened, in accordance with an embodiment of the present invention.
Figure 3:
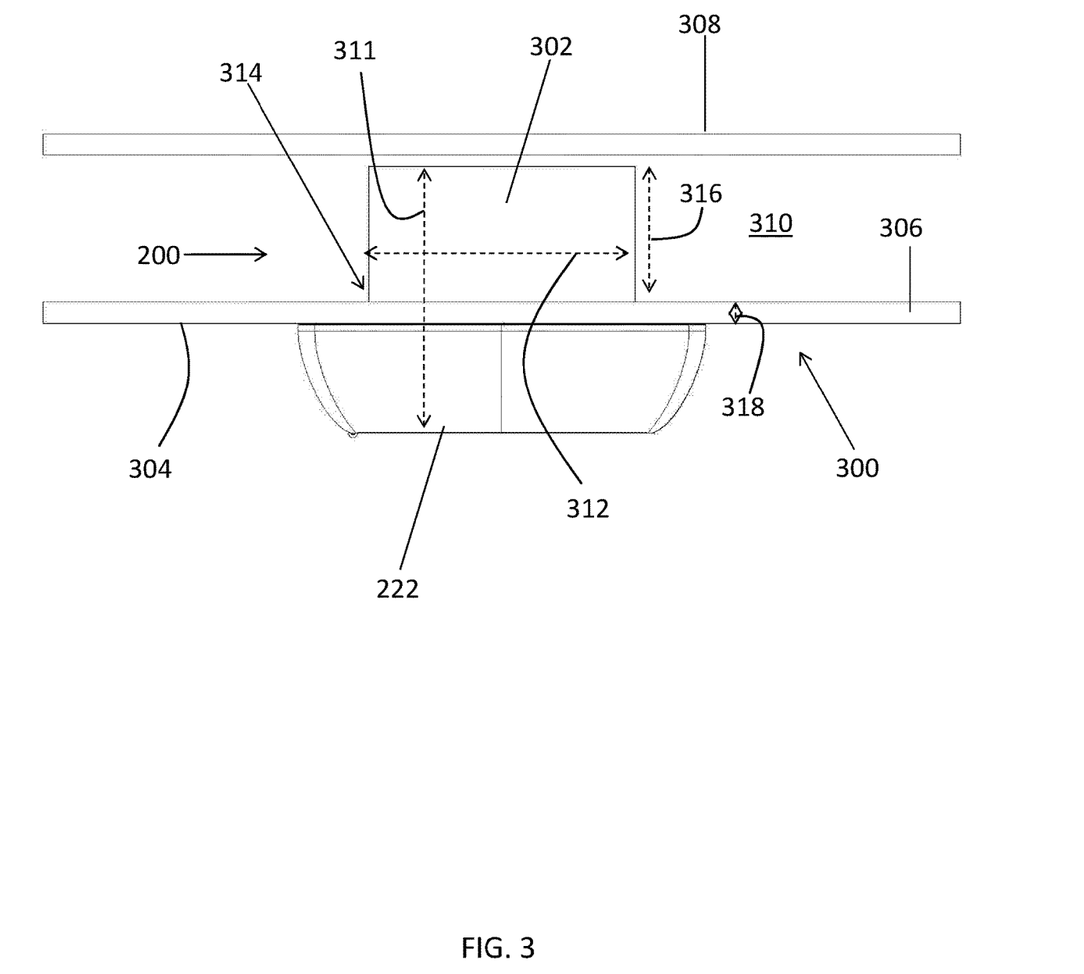
FIG. 3 is a top plan view of the toilet paper enclosure of FIG. 1, recessed within a building wall, in accordance with the present invention.

Referring now to FIGS. 1-3, one embodiment of the present invention is shown in a perspective view with a door opened, a perspective view with the door closed, and a top plan view, respectively. FIGS. 1-3 show several advantageous features of the present invention, but, as will be described below, the invention can be provided in several shapes, sizes, combinations of features and components, and varying numbers and functions of the components. The first example of a toilet paper dispenser 100, as shown in FIGS. 1-3, includes a wall mounted toilet paper dispensing body 200, at least one toilet paper roll support member 202, a light 204, and a door 206.

The wall mounted toilet paper dispensing body 200 can be considered a storage unit or housing for the toilet paper roll support member 202, the light 204, and one or more toilet paper roll rolls 208 disposed therein. The wall mounted toilet paper dispensing body 200 may be mounted to a building wall 300. In a preferred embodiment, the wall mounted toilet paper dispensing body 200 is entirely recessed within the building wall 300, as shown in FIG. 3. As used herein, the term "entirely recessed" means entirely recessed (i.e., 100% recessed) and substantially recessed, with the term "substantially recessed" meaning that at least 80% of the wall mounted toilet paper dispensing body 200 is recessed within the building wall 300. In other embodiments, the wall mounted toilet paper dispensing body 200 may be recessed within the building wall 300 in other proportions or percentages, such as at least 90% recessed within the building wall 300. In yet other embodiments, the wall mounted toilet paper dispensing body 200 may be at least 70% recessed within the building wall 300. In yet other embodiments, the wall mounted toilet paper dispensing body 200 may be recessed within the building wall at proportions/percentages outside of these ranges. Advantageously, in embodiments where the toilet paper dispensing body 200 is entirely recessed within the building wall 300, the area that would normally be occupied with a toilet paper dispenser, as in the existing art, is cleared and the toilet paper roll 208 is disposed farther away from a toilet bowl, which may reduce contaminant exposure.

In one embodiment, the wall mounted toilet paper dispensing body 200 may be a generally rectangular-shaped housing. Accordingly, the wall mounted toilet paper dispensing body 200 may a rear wall 210, two opposing side walls 212 and 214, a top wall 216 and an opposing bottom wall 218 disposed to form a generally rectangular-shaped toilet paper storage area. In other embodiments, the wall mounted toilet paper dispensing body 200 may be formed as other shapes and sizes, such as, for example, oval-shaped, circular-shaped, trapezoidal-shaped, square-shaped, and the like. In one embodiment, one or each of the walls 210, 212, 214, 216, and 218 of the wall mounted toilet paper dispensing body 200 may be made of a wood material. In other embodiments, one or each of the walls 210, 212, 214, 216, and 218 of the wall mounted toilet paper dispensing body 200 may be made of other materials, such as, for example, a metallic material, plastic, or other polymer or polymer-blend materials, and the like. In another embodiment, the wall mounted toilet paper dispensing body 200 may be 4.25 inches in length 311 and 4 inches in width 312. The height 226 of the wall mounted toilet paper dispensing body 200 may vary according to how many toilet paper rolls 208 the dispenser 100 is configured to house. In other embodiments, the wall mounted toilet paper dispensing body 200 may include dimensions outside of this range.

In one embodiment, the wall mounted toilet paper dispensing body 200 may include a main storage body 302 defining an open face 220. The assembly 100 may also include a frame 222 circumscribing a peripheral edge 224 of the main storage body 302 as best shown in FIG. 3. The frame 222 can be considered to frame the open face 220. The frame 222 acts as a flange to support and/or retain the body 200 to the building wall 300 by using, for example, one or more fasteners. In another embodiment, the frame 222 may be formed as a decorative fixture for the wall mounted toilet paper dispensing body 200. In yet another embodiment, the wall mounted toilet paper dispensing body 200 may not include the frame 222.

Referring now primarily to FIG. 3, an exemplary embodiment of the wall mounted toilet paper dispensing body 200 is shown recessed within the building wall 300. As can be seen in the exemplary embodiment, the main storage body 302 is entirely recessed within the building wall 300, with the frame 222 abutting a front surface 304 of the building wall 300. In one embodiment, the building wall 300 may include a first wall panel portion 306 and a second wall panel portion 308 separated by a clearance area 310 disposed between the first and second wall panel portions 306 and 308. The clearance area 310 may also be considered a recessed cavity 310 defined by the building wall 300. In a further embodiment, the second wall panel portion 308 may be disposed opposite the first wall panel portion 306. At least a portion of the wall mounted toilet paper dispensing body 200 may be disposed within the clearance area 310 between the first and second wall panel portions 306 and 308. In a further embodiment, the main storage body 302 may be disposed within the clearance area 310 between the first and second wall panel portions 306 and 308. In one embodiment, the entire main storage body 302 may be disposed within the clearance area 310 between the first and second wall panel portions 306 and 308. In another embodiment, at least 90% of the main storage body 302 may be disposed within the clearance area 310 between the first and second wall panel portions 306 and 308. In yet another embodiment, the disposition of the main storage body 302 within the clearance area 310 may be outside of these ranges.

In one embodiment, one or each of the first and second wall panel portions 306 and 308 may be a drywall panel. In yet another embodiment, one or each of the first and second wall panel portions 306 and 308 may be formed as another type of known building wall material. In yet a further embodiment, one or each of the first and second wall panel portions 306 and 308 may also include other materials known to be associated with building walls, such as, for example, insulation layers and the like. During installation of the toilet paper dispenser 100 within the building wall 300, a user or installer may cut an opening 314 through the first wall panel portion 306. The opening 314 may be sized and dimensioned to receive the wall mounted toilet paper dispensing body 200 (or at least the main storage body 302) therethrough and to permit the wall mounted toilet paper dispensing body 200 to be attached or coupled to the building wall 300, or, more specifically, to the first wall panel portion 306. The wall mounted toilet paper dispensing body 200 may be coupled to the first wall panel portion 306 by any known mechanism or method, such as, for example, an adhesive layer, adhesive strips, liquid nails, drywall clips, and other like fasteners. The main storage body 302 is the portion of the body 200 that spans a length 316 from a joint formed around the perimeter where the frame 222 joins the main body section 302 to the rear wall 210. As such, the main storage body 302 is disposed a length 316 behind a rear surface of the wall 300 less the thickness 318 of said wall.

Referring again primarily to FIGS. 2-3, the toilet paper roll support member 202 may be disposed within the wall mounted toilet paper dispensing body 200 so as to support the toilet paper roll 208 thereon. In one embodiment, the toilet paper roll support member 202 may be formed as a toilet paper rod. In a further embodiment, the toilet paper roll support member 202 may be formed as a collapsible toilet paper rod with a spring mechanism that allows the rod to be selectively collapsed or telescoped to adjust the length of the rod. This may permit the toilet paper roll 208 to be more readily removed and re-coupled to the wall mounted toilet paper dispensing body 200 for re-filling or exchanging the toilet paper roll 208. In other embodiments, the toilet paper roll support member 202 may be provided in other forms and configurations.

In one embodiment, the wall mounted toilet paper dispensing body 200 may be sized and dimensioned to house one toilet paper roll support member 202. In another embodiment, the wall mounted toilet paper dispensing body 200 may be sized and dimensioned to house two or more toilet paper roll support members 202 so as to support two or more toilet paper rolls 208 therein.

In one embodiment, the toilet paper roll support member 202 may be disposed within the wall mounted toilet paper dispensing body 200 such when the toilet paper roll 208 is supported on the toilet paper roll support member 202, less than 10% of the toilet paper roll 208 is disposed exterior to the building wall 300 when the wall mounted toilet paper dispensing body 200 is mounted to the building wall 300. More specifically, in a further embodiment, less than 10% of the toilet paper roll 208 may be disposed beyond a horizontal plane defined by the front surface 304 of the building wall 300. In other embodiments, the toilet paper roll support member 202 may be disposed within the wall mounted toilet paper dispensing body 200 such that when the toilet paper roll 208 is supported thereon, 0% of the toilet paper roll 208 is disposed exterior to the building wall 300. In other words, the toilet paper roll 208 may be completely disposed behind the building wall 300. In yet other embodiments, the toilet paper roll 208 may slightly protrude exterior to the building wall 300 outside of these ranges. In all embodiments, at least a substantial portion of the toilet paper rolls 208 housed within the wall mounted toilet paper dispensing body 200 should be disposed behind the building wall 300 and should be enclosed within the wall mounted toilet paper dispensing body 200, when the door 206 is closed, so as to prevent accidental contamination.

In one embodiment, the light 204 housed within the wall mounted toilet paper dispensing body 200 may be disposed to emit light rays toward the toilet paper roll 208 disposed on the toilet paper roll support member 202. More specifically, in a further embodiment, the light 204 is formed as an ultraviolet (UV) light disposed to emit UV rays 228 toward the toilet paper roll 208 disposed on the toilet paper roll support member 202. Advantageously, such UV rays 228 are sterilizing to the toilet paper roll 208, which may have become contaminated by various activities, including splash back from the toilet bowl during and after its use. The light 204 may be configured as a UV germicidal irradiation disinfection device that may use short-wavelength UV-C light to kill or inactivate microorganisms and bacteria.

In one embodiment, the light 204 may be coupled to an interior surface of the top wall 216 and oriented so as to emit UV light rays in a downward direction toward the toilet paper rolls 208 housed within the wall mounted toilet paper dispensing body 200. In one embodiment, the light 204 may be coupled to an interior surface of the rear wall 210 and oriented so as to emit UV light rays in a forward direction toward the toilet paper rolls 208 housed within the wall mounted toilet paper dispensing body 200. In yet another embodiment, the light 204 may be coupled to an interior surface of the bottom wall 218 and oriented to emit UV light rays in an upward direction towards the toilet paper rolls 208 housed within the wall mounted toilet paper dispensing body 200. In yet other embodiments, the light 204 may be mounted within the wall mounted toilet paper dispensing body 200 in other orientations and configurations.

In one embodiment, there may be one light 204 disposed within the wall mounted toilet paper dispensing body 200. In another embodiment, there may be two or more lights 204 disposed within the wall mounted toilet paper dispensing body 200. In a further embodiment, there may be one light 204 per toilet paper roll support member 202 such that one light 204 is oriented towards and dedicated towards disinfecting and sanitizing one toilet paper roll 208.

In other embodiments, the light 204 may not be a UV light, but may be formed as an LED light, an incandescent bulb, or another light source. In such embodiments, the light 204 may be primarily for illumination purposes, particularly for evening use, and not necessarily for sterilizing the toilet paper roll 208 with UV rays. Accordingly, in such embodiments, disposition and orientation of the light 204 within the wall mounted toilet paper dispensing body 200 is configured for illumination and may not necessarily be oriented to direct light rays at the toilet paper roll 208. In yet other embodiments, the sanitizing toilet paper dispenser 100 may not include the light 204. In another embodiment, the light 204 may be disposed external to the wall mounted toilet paper dispensing body 200.

Figure 6:
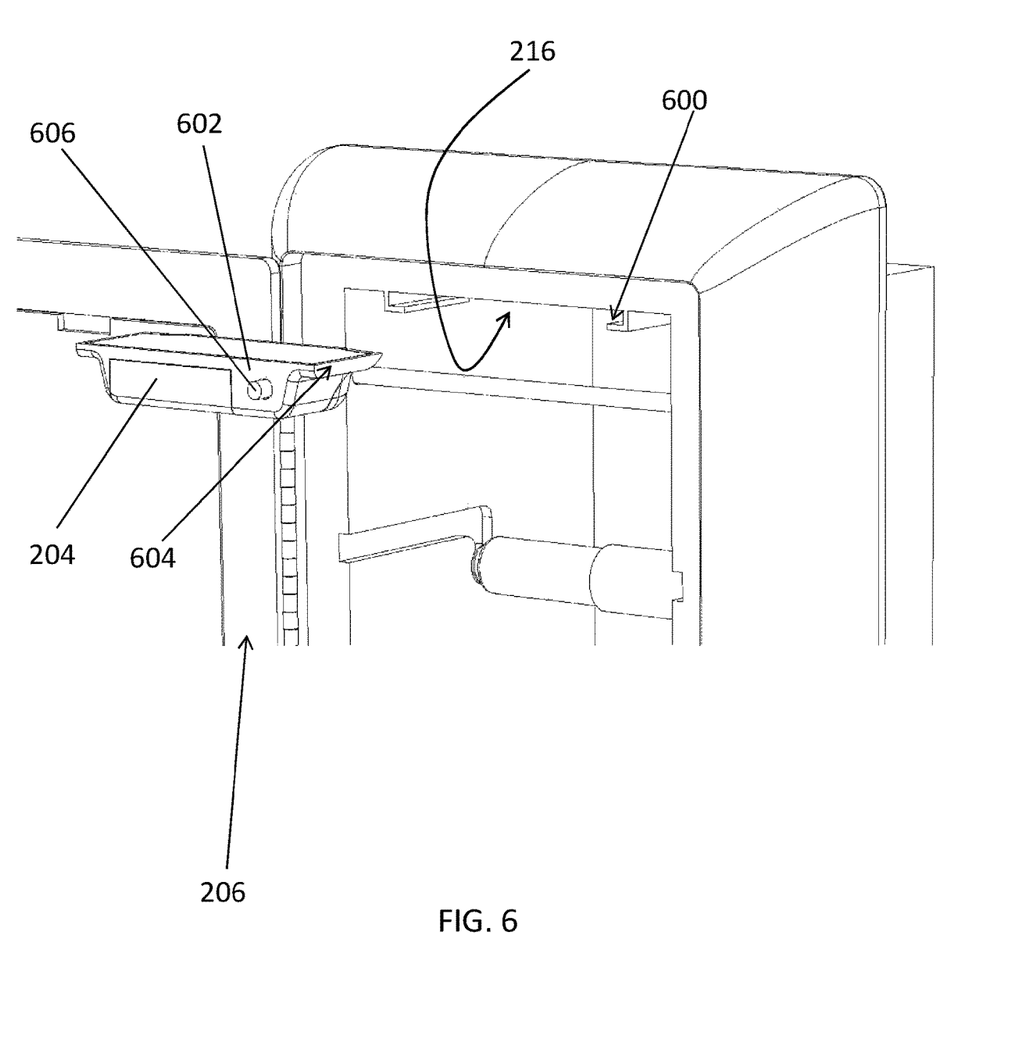
FIG. 6 is a fragmentary, enlarged view of the toilet paper enclosure of FIG. 1, illustrating a removable light, in accordance with the present invention.

Referring briefly to FIG. 6, the light 204 may be removeable from the wall mounted toilet paper dispensing body 200. In one embodiment, one of walls 210, 212, 214, 216, and 218 on which the light 204 is mounted may include a track 600 and the light 204 may include a light housing 602. The light housing 602 may include a pair of arms 604 (or protrusions) that are sized and dimensioned to engage the track 600 for selectively removing the light 204 and the light housing 602 from the wall mounted toilet paper dispensing body 200 for, for example, replacing the light 204 or a battery associated with the light 204. In other embodiments, the light 204 may be selectively removeable through other apparatuses and methods. The light housing 602 may include a button or other light actuator 606 operable to selectively turn the light 204 on and off. In a further embodiment, the actuator 606 may be coupled to a spring mechanism that automatically, by default, forces the actuator 606 outwardly to turn the light 204 on. The door 206 may be operable to depress the actuator 606 and automatically turn the light 204 off when the door 206 is securely closed/shut. Advantageously, such embodiment will serve to automatically turn the light 204 on when a user opens the door 206 to access the toilet paper roll 208 (see FIG. 2) and automatically turn the light 204 off when the user closes the door 206 shut, after use of the toilet paper roll 208.

Figure 7:
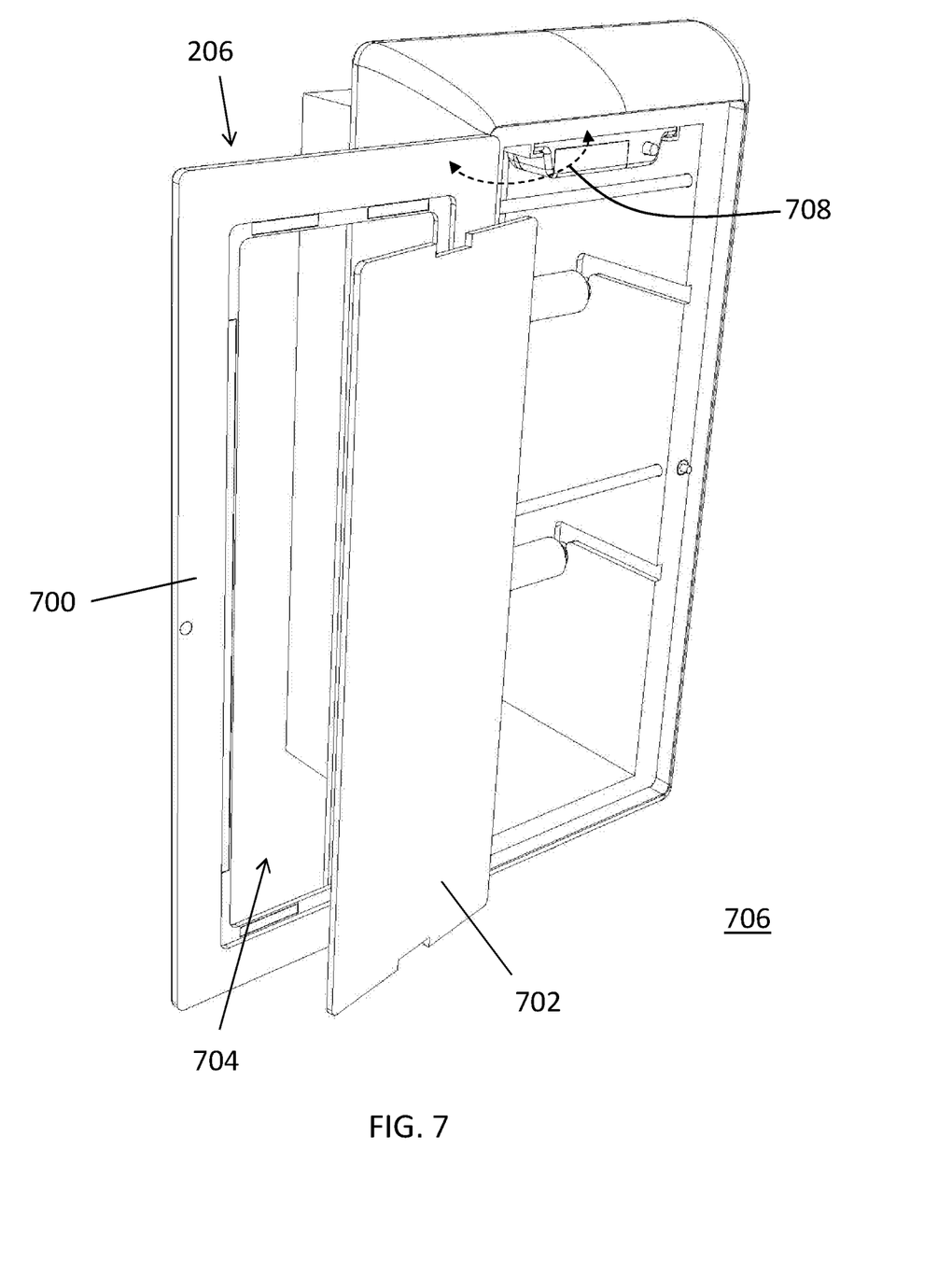
FIG. 7 is a front, perspective view of the toilet paper enclosure of FIG. 1, illustrating a removable decorative panel, in accordance with the present invention.

Referring again primarily to FIGS. 2-3, the door 206 advantageously forms a complete enclosure of the toilet paper rolls 208 within the wall mounted toilet paper dispensing body 200. In one embodiment, the door 206 may be hingedly coupled to a lateral edge 230 of the wall mounted toilet paper dispensing body 200 so as to form the enclosure that encloses the toilet paper roll support member 202, the toilet paper roll 208, and the light 204 therein when the door 206 is closed in a closed configuration. In other words, a hinge 232 may be disposed at the lateral edge 230 so as to permit the user to selectively open and close the door 206. The hinge 232 may define a vertical axis 234 disposed at the lateral edge 230 of the wall mounted toilet paper dispensing body 200 that may permit the door 206 to be rotatably openable and closeable about the vertical axis 234. Said differently, the door 206 forms an enclosure that encloses the at least one toilet paper roll support member 202 and the at least one toilet paper roll 208 when the door 206 is in a closed position (as best shown in FIG. 1) along a door translation path (an exemplary path 708 is shown in FIG. 7).

In yet other embodiments, the door 206 may be rotatably openable and closeable with other apparatuses and methods. Disposition at the lateral edge 230 of the toilet paper dispensing body 200 is distinguishable from existing toilet paper dispensers that have a top cover portion protruding from the dispenser. Such top cover portions would not be operable with embodiments of the present invention, which require that the toilet paper dispensing body 200 be recessed within the building wall 300. In other words, such existing top cover portions would not be accessible by the user behind the building wall 300. Accordingly, preferred embodiments of the present invention include the door 206 hingedly coupled at the side of the toilet paper dispensing body for permitting users to horizontally open and close the door 206.

In one embodiment, when the door 206 is closed in the closed configuration, the door 206 is disposed to be adjacent to and parallel with the building wall 300. In such embodiment, the door 206 may be formed as a flat, panel door. The door 206 may be rectangular-shaped. In other embodiments, the door 206 may be formed as other shapes and sizes, such as, for example, oval-shaped, circular-shaped, square-shaped, and the like. The door 206 should be sized and dimensioned to entirely cover or seal the open face 220 defined by the wall mounted toilet paper dispensing body 200 so as to form an enclosure when the door 206 is closed and to permit access into the wall mounted toilet paper dispensing body 200 through the open face 220 when the door 206 is opened. As used herein, the term "seal" is not intended to necessarily require an air-tight seal (although some embodiments may form an air-tight seal) but rather indicates that the open face 220 should be covered by the door 206 so as to prohibit contaminants from entering the wall mounted toilet paper dispensing body 200 to contaminate the toilet paper housed therein.

In one embodiment, the door 206 may be made of a wood material. In other embodiments, the door 206 may be made of other materials, such as, for example, a metallic material, plastic, or other polymer or polymer-blend materials, and the like. In one embodiment, the door 206 may be formed as a flat plate or panel. In other embodiments, the door 206 may be curve-shaped or have other cross-sections, shapes, and configurations, but should always be sized and dimensioned to cover the open face 220 to prohibit contaminants from soiling the toilet paper therein when the door 206 is closed.

In one embodiment, when the door 206 is closed, the door 206 may be considered to be disposed over the opening 314 defined by the building wall 300 such that the door 206 forms a seal over the opening 314 to enclose the toilet paper roll support member 202, the toilet paper roll 208, and the light 204 within the wall mounted toilet paper dispensing body 200 and behind the building wall 300. The opening 314 defined by the building wall 300 may be slightly larger than the open face 220 defined by the wall mounted toilet paper dispensing body 200.

Figure 4:
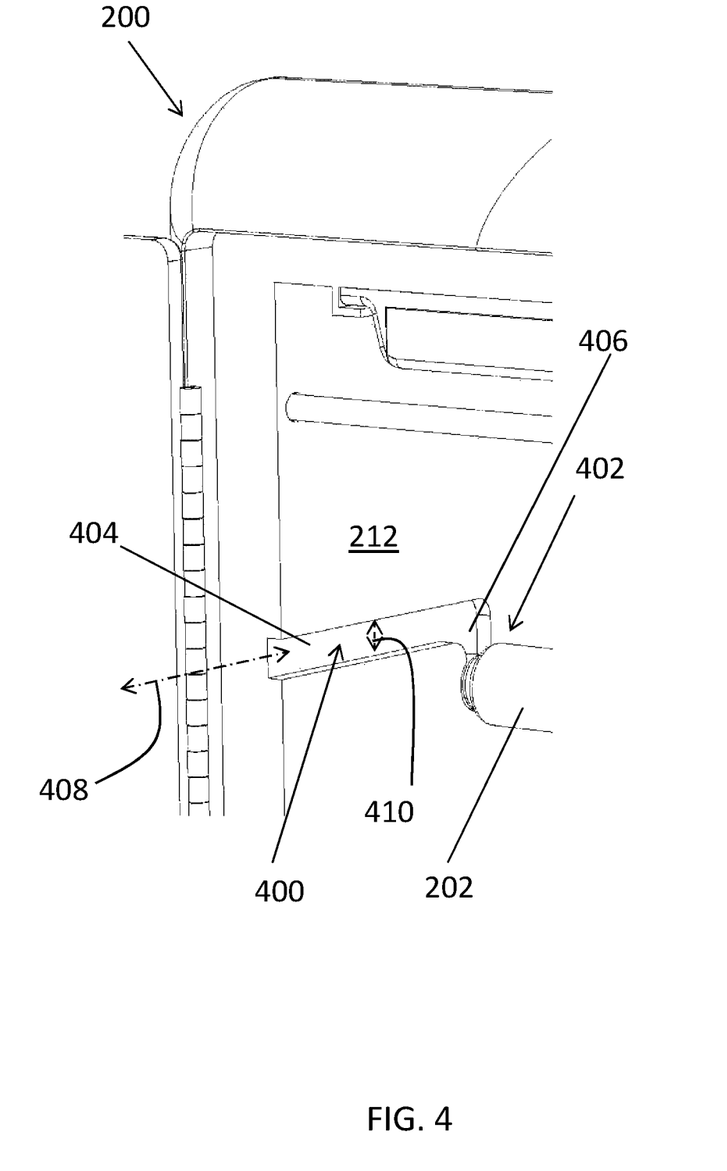
FIG. 4 is a fragmentary, enlarged view of the toilet paper enclosure of FIG. 1, illustrating a recessed channel, in accordance with the present invention.
Figure 5:
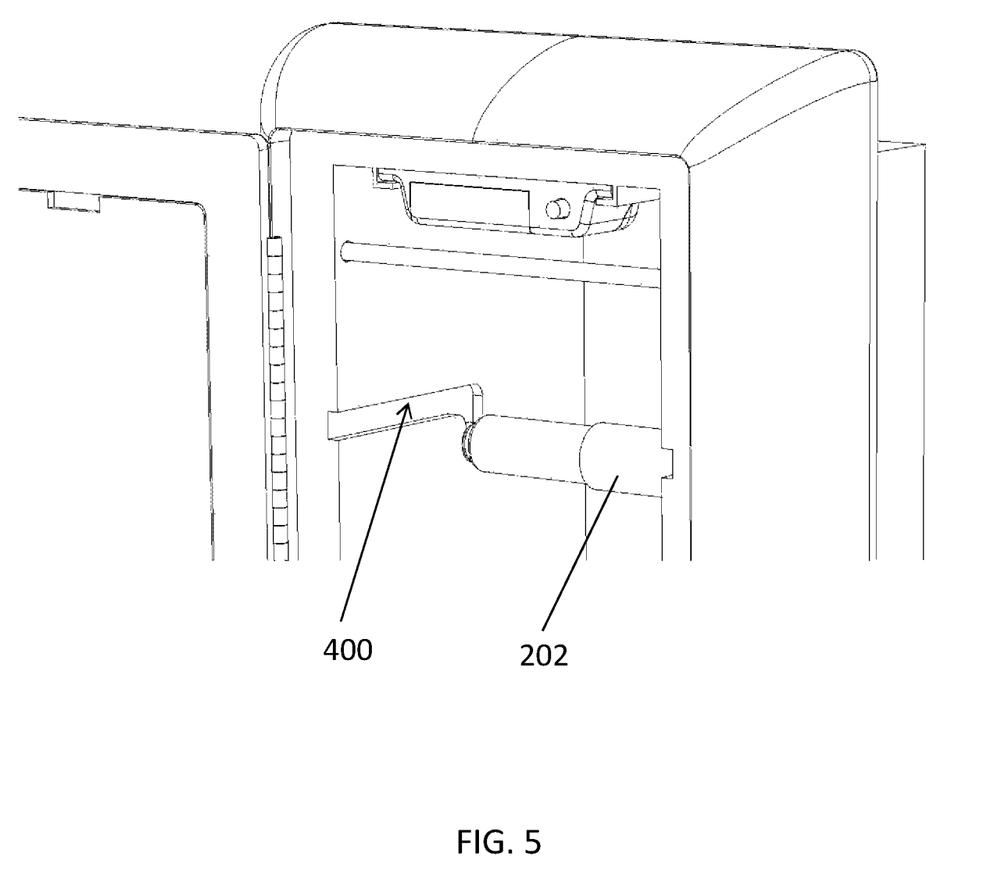
FIG. 5 is a fragmentary, enlarged view of the toilet paper enclosure of FIG. 1, illustrating the recessed channel, in accordance with the present invention.
Figure 8:
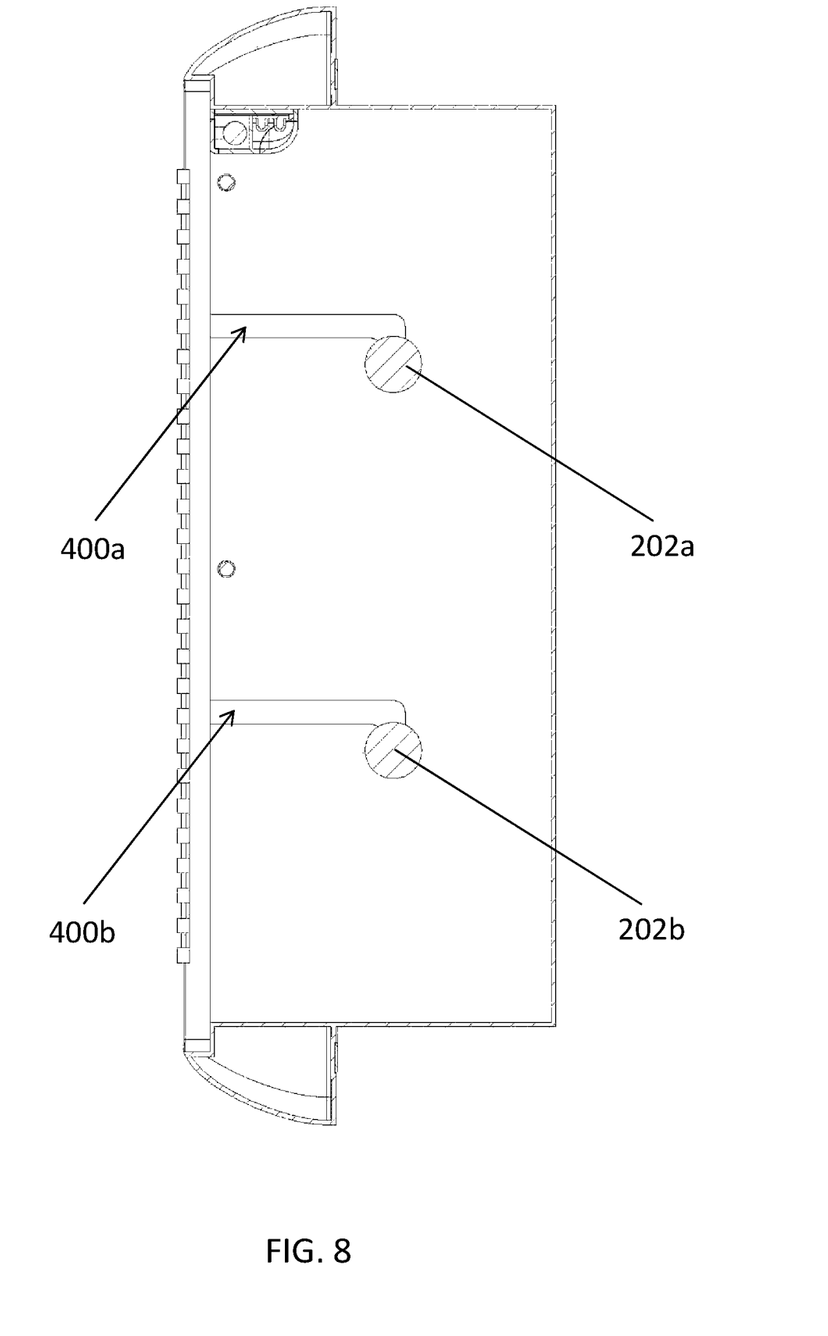
FIG. 8 is a side cross-sectional view of the toilet paper enclosure of FIG. 1, illustrating the recessed channels, in accordance with the present invention.

Referring now primarily to FIGS. 4-5, with brief reference to FIGS. 2-3, in one embodiment, the sidewalls 212 and 214 may each define a recessed channel 400. In a further embodiment, the recessed channel 400 may be sized and configured to slideably and frictionally receive an end 402 of the toilet paper roll support member 202 for securing the toilet paper roll support member 202 to the wall mounted toilet paper dispensing body 200. The end 402 of the toilet paper roll support member 202 may be formed as a neck portion of the toilet paper roll support member 202 that is slightly smaller than a main elongated body of the toilet paper roll support member 202. Although not shown in FIG. 4, it should be understood that the opposing end of the toilet paper roll support member 202, the opposing sidewall 214, and the recessed channel defined by the opposing sidewall 214, can be a mirror image of the end 402, the recessed channel 400, and the sidewall 212 depicted in FIG. 4. Furthermore, in embodiments with more than one toilet paper roll support member 202, there may be provided more than one recessed channel 400 on each sidewall 212 and 214. In the exemplary embodiment, which can be seen particularly clearly in FIG. 8, there are depicted two recessed channels 400a-b vertically spaced apart, on each sidewall 212 and 214, to support the two toilet paper roll support members 202a-b disposed within the wall mounted toilet paper dispensing body 200.

In one embodiment, the recessed channel 400 may be formed as an L-shaped channel. In another embodiment, the recessed channel 400 may be formed in other shapes and dimensions, such as, for example, a V-shaped channel, a curved-channel, a checkmark-shaped channel, a J-shaped channel, and the like. In a preferred embodiment, the recessed channel 400 may be considered to include a first channel portion 404 and a second channel portion 406. The first channel portion 404 may be disposed to permit movement of the toilet paper roll support member 202 in directions 408 towards and away from the building wall 300 and the second channel portion 406 may be disposed to restrict movement of the toilet paper roll support member 202 in the directions 408 towards and away from the building wall 300. In other words, the first channel portion 404 may be disposed and oriented so as to permit the user to remove and re-couple the toilet paper roll support member 202 to the wall mounted toilet paper dispensing body 200 for resupplying the sanitizing toilet paper dispenser 100 with new toilet paper rolls 208. Further, the second channel portion 406 may be disposed and oriented so as to not permit the toilet paper roll support member 202 to be removed or uncoupled. In other words, the second channel portion 406 may secure or lock the toilet paper roll support member 202 to the wall mounted toilet paper dispensing body 200, where otherwise it may risk rolling out of the recessed channel 400 or otherwise become unsecured. In one embodiment, the first channel portion 404 and the second channel portion 406 may be continuous with one another. In another embodiment, the first channel portion 404 and the second channel portion 406 may be dimensioned with the same channel width 410. The channel width 410 may be sized to frictionally receive the end 402 or neck portion of the toilet paper roll support member 202. In an alternative embodiment, the first and second channel portions 404 and 406 may be formed with other dimensions and configurations.

Figure 9:
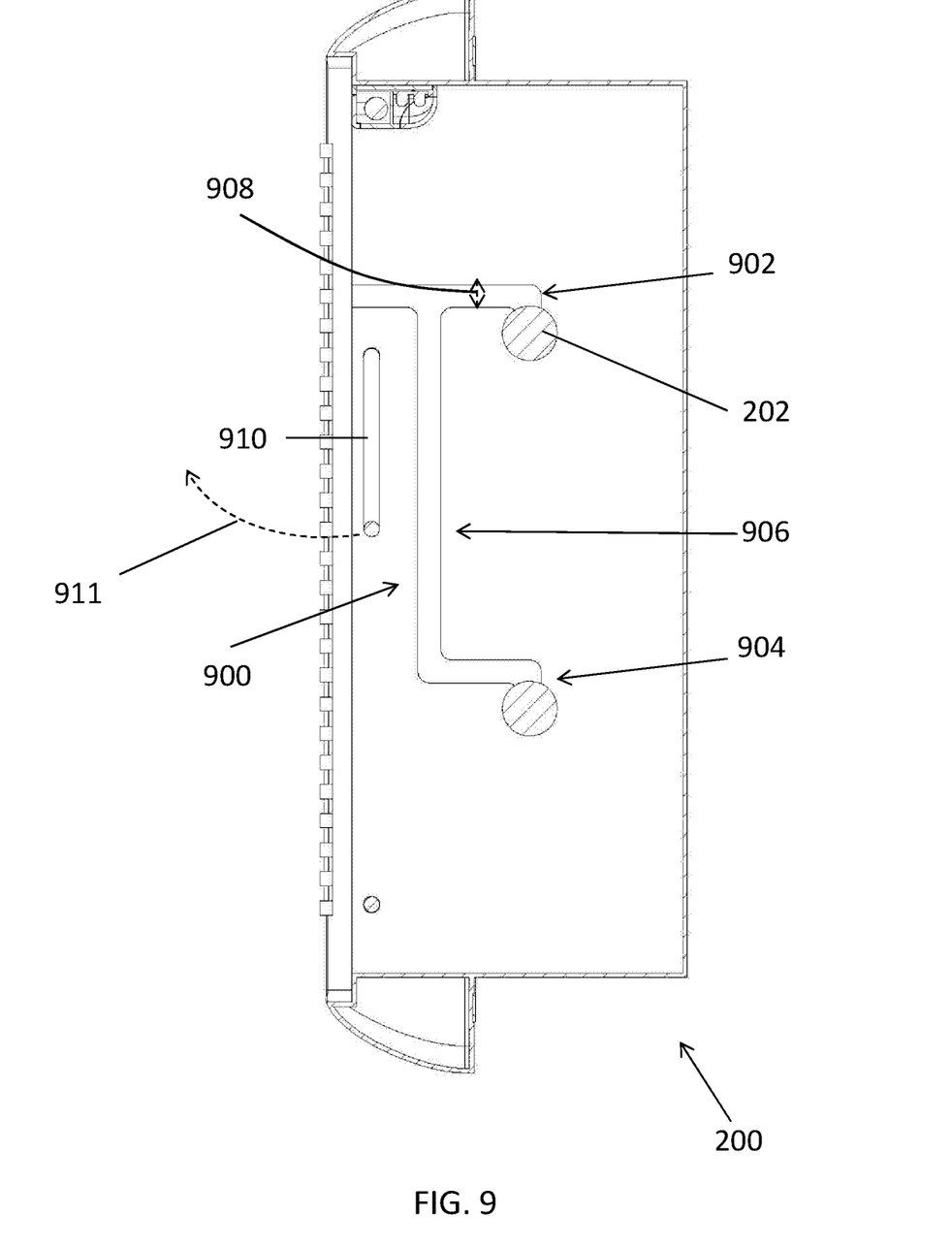
FIG. 9 is a side cross-sectional view of the toilet paper enclosure of FIG. 1, illustrating an alternative embodiment recessed channel, in accordance with the present invention.
Figure 10:
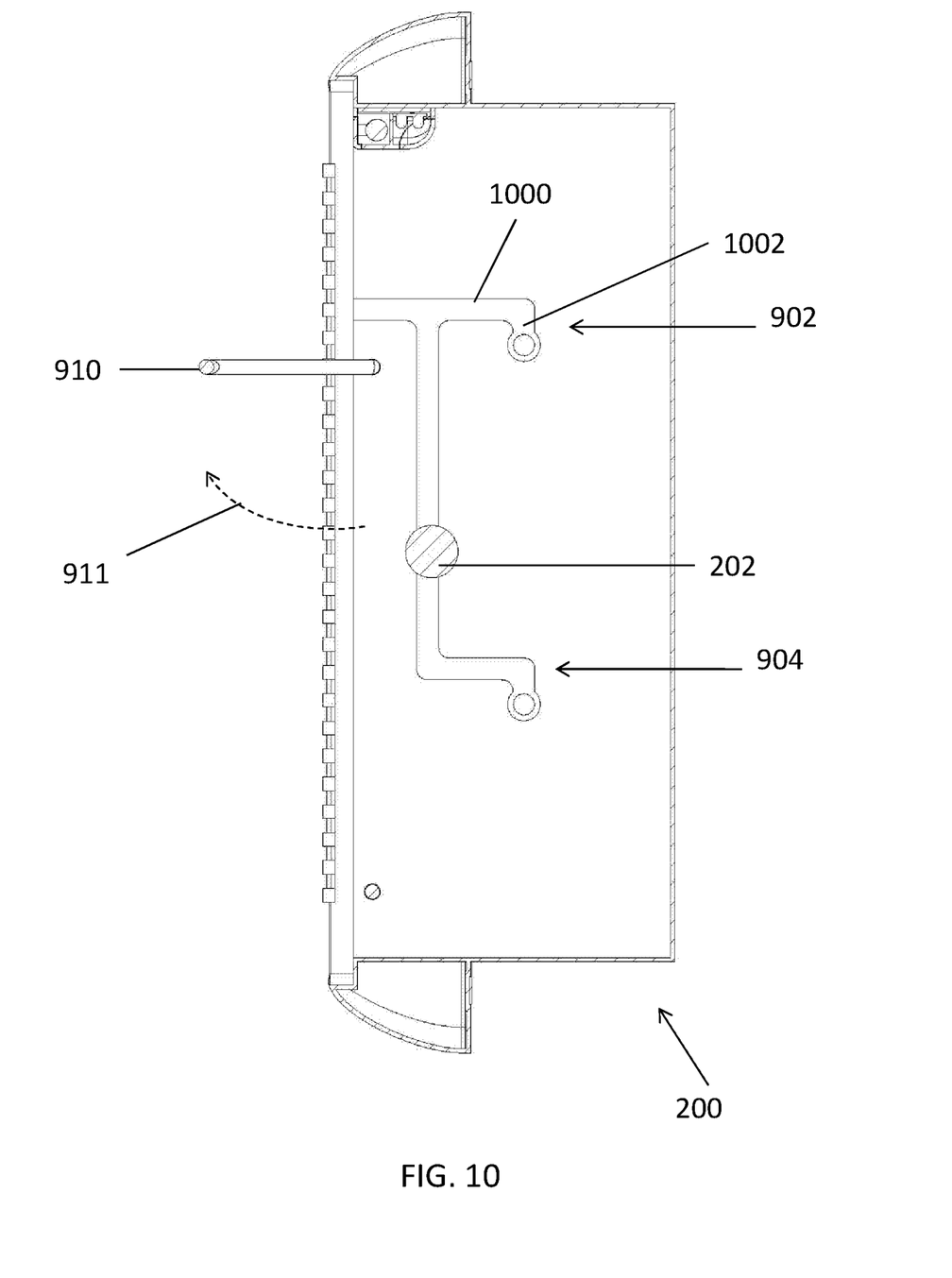
FIG. 10 is a side cross-sectional view of the toilet paper enclosure of FIG. 1, illustrating the alternative embodiment recessed channel with a pivoting toilet paper feed rod, in accordance with the present invention.

Referring now briefly to FIGS. 9-10, with brief reference to FIGS. 2-3, in one embodiment, the wall mounted toilet paper dispensing body 200 includes a multiple toilet paper roll recessed channel 900. More specifically, in one embodiment, the sidewalls 212 and 214 may each define a multiple toilet paper roll recessed channel 900. The multiple toilet paper roll recessed channel 900 may be a continuous channel that can be used to selectively remove and secure more than toilet paper roll support member 202 to the wall mounted toilet paper dispensing body 200. In one embodiment, the multiple toilet paper roll recessed channel 900 may be formed to include more than one L-shaped channel. In another embodiment, the multiple toilet paper roll recessed channel 900 may include other shaped channels. In a preferred embodiment, the multiple toilet paper roll recessed channel 900 may include a first recessed channel portion 902, a second recessed channel portion 904, and an intermediate recessed channel portion 906 disposed between the first and second recessed channel portions 902 and 904. In a further embodiment, the first, second, and intermediate recessed channel portions 902, 904, and 906 may be continuous with one another. In yet a further embodiment, each of the first, second, and intermediate recessed channel portions 902, 904, and 906 may be dimensioned to have the same channel width 908.

In one embodiment, each of the first and second recessed channel portions 902 and 904 may include a first channel portion 1000 and a second channel portion 1002. In one embodiment, the first channel portion 1000 may be disposed to permit movement of the toilet paper roll support member 202 in directions towards and away from the building wall 300 and the second channel portion 1002 may be disposed to restrict movement of the toilet paper roll support member 202 in the directions towards and away from the building wall 300. In other words, the first channel portion 1000 may be disposed and oriented so as to permit the user to remove and re-couple the toilet paper roll support member 202 to the wall mounted toilet paper dispensing body 200 for resupplying the sanitizing toilet paper dispenser 100 with new toilet paper rolls 208. Further, the second channel portion 1002 may be disposed and oriented so as to not permit the toilet paper roll support member 202 to be removed or uncoupled. In other words, the second channel portion 1002 may secure or lock the toilet paper roll support member 202 to the wall mounted toilet paper dispensing body 200, where otherwise it may risk rolling out of the multiple toilet paper roll recessed channel 900 or otherwise become unsecured. In one embodiment, the channel width 908 may be sized to frictionally receive the end 402 or neck portion of the toilet paper roll support member 202. In an alternative embodiment, the first and second channel portions 1000 and 1002 may be formed with other dimensions and configurations.

Referring again primarily to FIG. 2, in one embodiment, there may be provided a toilet paper feed member 236 coupled to and housed within the wall mounted toilet paper dispensing body 200. The toilet paper feed member 236 may be considered a support member for a free end of a toilet paper panel that may support the free end of the toilet paper panel thereon for permitting the user to readily grip the free end for use. Users sometimes have trouble locating the free end of the toilet paper roll 208 so that a section of the toilet paper panel can be pulled and torn off for use. Advantageously, providing the toilet paper feed member 236 to support the free end and have it ready for access by the user can save such users the time and hassle of locating the free end.

In one embodiment, the toilet paper feed member 236 may be formed as a rod. In a further embodiment, the toilet paper feed member 236 may be attached, fastened, or otherwise coupled, at each opposing end of the member 236, to a respective sidewall 212 and 214. In another embodiment, there may be provided more than one toilet paper feed member 236 within the wall mounted toilet paper dispensing body 200. In one embodiment, there may be provided one toilet paper feed member 236 corresponding to each toilet paper roll support member 202 disposed within the wall mounted toilet paper dispensing body 200. In yet another embodiment, each toilet paper feed member 236 may be disposed beneath the toilet paper roll 208 supported on the corresponding toilet paper roll support member 202. In yet another embodiment, each toilet paper feed member 236 may be disposed above the toilet paper roll 208 supported on the corresponding toilet paper roll support member 202.

Referring now primarily again to FIGS. 9-10, with brief reference to FIG. 2, in one embodiment, there may be provided a pivoting toilet paper feed member 910. In one embodiment, the pivoting toilet paper feed member 910 may be formed as a U-shaped member. In another embodiment, the pivoting toilet paper feed member 910 may be formed as other shapes and sizes, such as, for example, V-shaped, half-square-shaped, and the like. In yet another embodiment, the pivoting toilet paper feed member 910 may be rod-like, having a circular cross-section along its length. The pivoting toilet paper feed member 910 may be pivotably coupled to the wall mounted toilet paper dispensing body 200. More specifically, in one embodiment, the pivoting toilet paper feed member 910 may be pivotably coupled to each sidewall 212 and 214 of the wall mounted toilet paper dispensing body 200 so as to be selectively pivoted by the user, along a pivoting path 911, towards and away from the toilet paper roll 208 supported on the toilet paper roll support member 202. Advantageously, this permits users to move the toilet paper feed member 910 out of the way to provide a clearance to access the free end of the toilet paper panel on the toilet paper roll 208 so that the user can then feed or support the free end on the toilet paper feed member 910. Otherwise, it may be difficult for the user to initially identify and feed the free end of the toilet paper roll 208 on the toilet paper feed member 910. FIG. 9 illustrates the pivoting toilet paper feed member 910 disposed towards the toilet paper roll support member 202. FIG. 10 illustrates the pivoting toilet paper feed member 910 selectively pivoted, along the pivoting path 911, upwardly and away from the toilet paper roll support member 202.

Referring now primarily to FIG. 7, with brief reference to FIGS. 2-3, in one embodiment, the door 206 may include a door frame portion 700 and a plate portion 702. As used herein, the term "plate" is intended to indicate a flat, thin sheet or layer of material. The door frame portion 700 may be shaped, dimensioned, and otherwise configured to matingly, removeably couple to the plate portion 702. Advantageously, users can select from a variety of plate portions 702 with varying designs, patterns, materials, etc. Specifically, existing toilet paper dispensers do not allow for visual variety and interchangeability. If a user desires a different look for the toilet paper dispenser, the user is normally required to purchase another dispenser that looks differently. However, embodiments of the present invention allow users to change out plate portions 702 to match their wall color/pattern/material, or for other purposes. The plate portions 702 may be provided in various designs, such as, for example, a glass sheet, a mirror, a smooth texture, a textured surface, a marble or faux marble finish, a decorative tile plate, a solid colored plate, a wood or faux wood finish, and the like. In other embodiments, the plate portions 702 may include a magnet with a plurality of magnetic pieces to form a puzzle or other entertaining feature that may entertain the user while he or she is utilizing the toilet bowl. In yet another embodiment, the plate portion 702 may form a pocket that may receive magazines or books that may also entertain the user during use of the toilet bowl. The plate portion 702 may be rectangular-shaped. In another embodiment, the plate portion 702 may be square-shaped, trapezoidal shaped, triangular-shaped, oval-shaped, and the like. In yet other embodiments, the plate portion 702 may be provided in yet other configurations. Advantageously, such plate portions 702 provide an added flexibility and interchangeability of design, while also providing a secure sanitizing enclosure for the toilet paper rolls 208 disposed therein.

In one embodiment, the door frame portion 700 may define an aperture 704. The aperture 704 may be dimensioned to receive the plate portion 702 so as to reveal all or at least a substantial portion of the plate portion 702 to an external environment 706, more specifically, to users within a bathroom. In one embodiment, the aperture 704 may be shaped similar to and dimensioned slightly smaller than the plate portion 702 such that only the peripheral edge of the plate portion 702 may be disposed behind the door frame portion 700. In other embodiments, the aperture 704 may be shaped differently than the plate portion 702 but should still be configured to reveal all or at least a substantial portion of the plate portion 702 to the external environment 706 for aesthetic viewing pleasure.

In one embodiment, the door frame portion 700 may be shaped similar to and dimensioned similar to the plate portion 702. In another embodiment, the door frame portion 700 may be shaped and dimensioned differently than the plate portion 702. In one embodiment, the door frame portion 700 may form a rectangular-shaped outline or frame. In another embodiment, the door frame portion 700 may form a square-shaped, trapezoidal shaped, triangular-shaped, oval-shaped, and other shaped outlines or frames. Importantly for such embodiments with door frame and plate portions, the plate portion 702 should be removeably couplable to the door frame portion 700 such that when the plate portion 702 is coupled to the door frame portion 700, the door 206 forms the enclosure when the door 206 is closed. There should be no apertures or other access points or openings into the wall mounted toilet paper dispensing body 200 when the door 206 is closed so as to restrict the entry of any contaminates during use of the toilet bowl.

The door frame portion 700 may be couplable to the plate portion 702 in a variety of methods and apparatuses. In one embodiment, the door frame portion 700 may include a plurality of track or track portions that are dimensioned and configured to receive portions of the plate portion 702 therein for securing the plate portion 702 to the door frame portion 700. In another embodiment, the door frame portion 700 may be selectively coupled to the plate portion 702 by one or more magnets. In yet another embodiment, the door frame portion 700 may include one or more tabs or swing arms that may be selectively secured over the plate portion 702 to fasten the plate portion 702 to the door frame portion 700. In yet other embodiments, the door frame portion 700 may be selectively couplable to the plate portion 702 with other types of fastening mechanisms.

A novel and efficient sanitizing toilet paper dispenser. Embodiments of the invention provide a wall mounted toilet paper dispensing body that is at least substantially recessed within a building wall. In addition, embodiments of the invention provide at least one toilet paper roll supporting rod, and a door hingedly coupled to the wall mounted toilet paper dispensing body that forms an enclosure for the rod and the toilet paper roll when the door is closed. Further embodiments of the present invention also include a UV light enclosed within the wall mounted toilet paper dispensing body to sanitize the toilet paper roll. Other embodiments of the present invention provide for recessed channels within sidewalls of the wall mounted body that permit movement of the rod in one direction for receiving the rod into the enclosure and that restricts movement of the rod in another direction for locking the rod into the enclosure. Additional embodiments include a novel and non-obvious toilet paper feed rod disposed above or beneath the toilet paper roll and operable to support a free end of a toilet paper panel for permitting the user to readily grip the free end when use is desired. Embodiments of the present invention also include a door frame and a plate portion that allows decorative plates to be interchangeable to provide decorative variety to users and to allow users to match the toilet paper enclosure to the user's wall or floor.

What is claimed is:

1. A sanitizing toilet paper dispenser comprising:
   a building wall;
   a toilet paper dispensing body entirely recessed within the building wall;
   at least one toilet paper roll support member disposed within the toilet paper dispensing body to support at least one toilet paper roll thereon; and
   a door:
     including a door frame portion and a plate portion, the door frame portion defining an aperture dimensioned to reveal the plate portion to an external environment and the plate portion removeably couplable to the door frame portion;
     hingedly coupled to an edge of the toilet paper dispensing body so to so as to be rotatably openable and forming an enclosure that encloses the at least one toilet paper roll support member and the at least one toilet paper roll when the door is closed and the plate portion is coupled to the door frame portion; and
   a UV light disposed to emit UV rays toward the at least one toilet paper roll disposed on the at least one toilet paper roll support member, wherein the UV light is mounted on tracks in the toilet paper dispensing body and is removable from the tracks, and wherein the UV light includes a button switch at a front of the UV light that is configured to be actuated by contact with the door and further configured to turn on when the door is opened and breaking contact with the button switch.

2. The sanitizing toilet paper dispenser in accordance with claim 1, wherein:
   the UV light is battery powered.

3. The sanitizing toilet paper dispenser in accordance with claim 1, wherein:
   the wall mounted toilet paper dispensing body defines an open face into the enclosure when the door is opened; and
   the door is dimensioned to entirely cover the open face to seal the enclosure when the door is closed.

4. The sanitizing toilet paper dispenser in accordance with claim 1, wherein:
   the wall mounted toilet paper dispensing body includes a pair of opposing sidewalls, each of the pair of opposing sidewalls recessed within the building wall and defining a recessed channel disposed to slideably and frictionally receive an end of the at least one toilet paper roll support member therein for securing the at least one toilet paper roll support member to toilet paper dispensing body.

5. The sanitizing toilet paper dispenser in accordance with claim 4, wherein:
   the recessed channel for each of the pair of opposing sidewalls includes a first channel portion and a second channel portion, the first channel portion disposed to permit movement of the at least one toilet paper roll support member in a direction toward the building wall and the second channel portion disposed to restrict movement of the at least one toilet paper roll support member in the direction toward the building wall.

6. The sanitizing toilet paper dispenser in accordance with claim 1, further comprising:
   at least one toilet paper feed member coupled to the toilet paper dispensing body so as to be disposed at least one of above and beneath the at least one toilet paper roll supported on the at least one toilet paper roll support member and operable to support a free end of a toilet paper panel of the at least one toilet paper roll for readily gripping by a user when the door is opened.

7. A sanitizing toilet paper dispenser comprising:
   a wall mounted toilet paper dispensing body recessed within a building wall;
   at least one toilet paper roll support member disposed within the wall mounted toilet paper dispensing body to support at least one toilet paper roll thereon;

a UV light disposed to emit UV rays toward the at least one toilet paper roll disposed on the at least one toilet paper roll support member;

a door:

including a door frame portion and a plate portion, the door frame portion defining an aperture dimensioned to reveal the plate portion to an external environment and the plate portion removeably couplable to the door frame portion; and hingedly coupled to an edge of the wall mounted toilet paper dispensing body so to so as to be rotatably openable and forming an enclosure that encloses the at least one toilet paper roll support member, the at least one toilet paper roll, and the UV light when the door is closed and the plate portion is coupled to the door frame portion; and at least one toilet paper feed member coupled to the wall mounted toilet paper dispensing body so as to be disposed at least one of above and beneath the at least one toilet paper roll supported on the at least one toilet paper roll support member and operable to support a free end of a toilet paper panel of the at least one toilet paper roll for readily gripping by a user when the door is opened;

wherein the UV light is mounted on tracks in the toilet paper dispensing body and is removable from the tracks, and wherein the UV light includes a button switch at a front of the UV light that is configured to be actuated by contact with the door and further configured to turn on when the door is opened and breaking contact with the button switch.

8. The sanitizing toilet paper dispenser in accordance with claim 7, wherein:

the edge is a lateral edge; and the door is further hingedly coupled to the lateral edge of the toilet paper dispensing body so as to be rotatably openable about a vertical axis defined by a hinge disposed at the lateral edge.

9. The sanitizing toilet paper dispenser in accordance with claim 7, further comprising:

when the door is closed, the door is disposed over an opening defined by the building wall into which the wall mounted toilet paper dispensing body is recessed such that the door forms a seal over the opening to enclose the at least one toilet paper roll support member, the at least one toilet paper roll, and the UV light within the wall mounted toilet paper dispensing body and behind the building wall.

10. A sanitizing toilet paper dispenser comprising:

a wall mounted toilet paper dispensing body;

at least one toilet paper roll support member disposed within the wall mounted toilet paper dispensing body to support at least one toilet paper roll thereon;

a UV light disposed to emit UV rays toward the at least one toilet paper roll disposed on the at least one toilet paper roll support member;

a door including a door frame portion hingedly coupled to an edge of the wall mounted toilet paper dispensing body so to so as to be rotatably openable and forming an enclosure that encloses the at least one toilet paper roll support member, the at least one toilet paper roll, and the UV light when the door is closed and the plate portion is coupled to the door frame portion; and at least one toilet paper feed member coupled to the wall mounted toilet paper dispensing body so as to be disposed at least one of above and beneath the at least one toilet paper roll supported on the at least one toilet paper roll support member and operable to support a free end of a toilet paper panel of the at least one toilet paper roll for readily gripping by a user when the door is opened;

wherein the UV light is mounted on tracks in the toilet paper dispensing body and is removable from the tracks, and wherein the UV light includes a button switch at a front of the UV light that is configured to be actuated by contact with the door and further configured to turn on when the door is opened and breaking contact with the button switch.

\* \* \* \* \*